(12) United States Patent  
Goods et al.

(10) Patent No.: US 6,581,474 B2  
(45) Date of Patent: Jun. 24, 2003

(54) TRIBOLUMINESCENT INDICATOR SYSTEM

(75) Inventors: Steven H. Goods, Livermore, CA (US);  
Paul M. Dentinger, Sunol, CA (US);  
Leroy L. Whinnery, Jr., Danville, CA (US)

(73) Assignee: Sandia National Laboratories, Livermore, CA (US)

( * ) Notice: Subject to any disclaimer, the term of this patent is extended or adjusted under 35 U.S.C. 154(b) by 0 days.

(21) Appl. No.: 09/792,670

(22) Filed: Feb. 22, 2001

(65) Prior Publication Data

US 2002/0148300 A1 Oct. 17, 2002

(51) Int. Cl.⁷ ............................................. G01L 1/24
(52) U.S. Cl. ........................................................ 73/800
(58) Field of Search ........................... 73/800, 762, 763, 73/862.324, 862.624

(56) References Cited

U.S. PATENT DOCUMENTS

| | | | | |
|---|---|---|---|---|
| 4,020,765 A | * | 5/1977 | Glass et al. ................... | 102/201 |
| 5,581,082 A | * | 12/1996 | Hansma et al. .............. | 250/306 |
| 5,905,260 A | | 5/1999 | Sage et al. ................... | 250/306 |
| 6,071,632 A | | 6/2000 | Hall-Goulle ................. | 428/690 |
| 6,270,117 B1 | * | 8/2001 | Storey ......................... | 250/221 |

* cited by examiner

*Primary Examiner*—Max Noori  
(74) *Attorney, Agent, or Firm*—Timothy P. Evans

(57) ABSTRACT

There is provided a light emitting device comprising a plurality of triboluminescent particles dispersed throughout a low density, frangible body and activated by rapidly crushing the body in order to transfer mechanical energy to some portion of the particles. The light emitted by these mechanically excited particles is collected and directed into a light conduit and transmitted to a detector/indicator means.

22 Claims, 10 Drawing Sheets

TRIBOLUMINESCENT INDICATOR SYSTEM

The United States Government has rights in this invention pursuant to Contract No. DE-AC04-94AL85000 between the United States Department of Energy and Sandia Corporation for the operation of Sandia National Laboratories.

BACKGROUND OF THE INVENTION

1. Field of the Invention

This invention relates generally to systems and devices for sensing high accelerations or impact events. The invention is particularly drawn to providing systems and devices incorporating certain compounds, known to produce light radiation when subjected to mechanical energy and to systems and devices wherein these compounds are dispersed throughout a frangible porous material.

2. Statement of the Problem

Under certain circumstances, it is desirable to provide a mechanical or electrical system with embedded sensor/indicators which are, and remain, electrically isolated, and do not rely on sources of electrical power for activation. This is because there is a desire to prevent compromise to the safety or integrity of the system through an external power supply connector, to prevent unauthorized access, or to avoid the need for entry into the system in order to periodically replace limited life reserve sources of electrical energy.

An indicating sensor providing a pulse of detectable light would be a useful method for verifying whether or not various internal system functions have activated, or whether or not certain parameters of in the internal system environments had been exceeded. Events such as movement of mechanical actuators, pistons, or gears, the activation of an explosive actuator, acceleration loads such as impact events (beyond a predetermined level), and the like, are examples of binary threshold events to which a shock-sensitive indicator device could be applied.

It is known that all bodies radiate electromagnetic energy, so-called black body radiation or thermal emission, i.e., "heat." That is, hot bodies that are self-luminous solely because of their high temperature represent a special case and are said to emit visible light by incandescent radiation. All other forms of light emission are said to be luminescent and are dependent upon the specific material. The luminescence process itself involves 1.) absorption of energy; 2.) excitation; and 3.) emission of energy, usually in the form of radiation in the visible part of the spectrum. Therefore, some source of energy is required in order to trigger and/or to continue light emission since such emissions represent a net loss of energy by the body. Most of these kinds of luminescence are classified according to the source from which this energy is derived, e.g., the light from a gas discharge lamp, produced by the passage of an electric current through the ionized gas is said to be electroluminescent.

In particular, light which results from energy supplied to a material in the form of mechanical energy, is known as triboluminescence; also referred to as mechano-luminescence or fracto-luminescence. The effect is thought to arise through fracture or cleavage of individual crystals of a certain class of solid materials together with a concomitant electrical breakdown. However, the effect is poorly understood and may be the result of any input of mechanical energy which provides frictional force, or some amount of strain energy, to a particle of the identified class of materials, even of non-crystalline materials. Furthermore, the effect may arise also as the result of an electric charge separation as new interfacial surface is created as the material is either cleaved or breaks free and separates from a surrounding host matrix in which the material is embedded. In either case, it is known that when mechanical energy is imparted to certain compounds these compounds emit light energy and that this effect is intense enough in certain materials to be easily detectable. The observed range of light wavelengths runs from red to deep ultraviolet.

3. The Prior Art

While triboluminescence is a well known phenomenon, its application to physical sensors is limited. U.S. Pat. No. 4,020,765 to Glass, et al., describes a munitions fuse relying upon a light signal generated by ordnance of a triboluminescent material coating the inside of the ordnance nosecone as the ordnance strikes a target. U.S. Pat. No. 5,905,260 to Sage, et al., describes a sensor for detecting damage in aircraft structures by connecting a piece of light guiding optical fiber with a triboluminescent material. Damage to the structure is recorded by light pulses generated by fracture of a plurality of triboluminescent crystals. Neither of these patents, however, describe a sensor-indicator comprising a comminuted, triboluminescent powder dispersed within a frangible media material.

SUMMARY OF THE INVENTION

Triboluminescent light may be useful where there is a need to record the response to a mechanical event without the need for relying upon a source of electrical power.

A principal object of the present invention is to provide systems and devices incorporating triboluminescent constituents for providing a transient source of light emission.

Another object of this invention is to provide a systems and a device for generating a source of light emission which is subsequently converted into an electrical signal.

A further object of this invention is to provide means for containing one or more triboluminescent constituent materials and means for suspending said materials in a low density, frangible solid media.

This invention comprises a device for providing a light indicator display comprising a triboluminescent compound. The device comprises a frangible foam substrate within which the triboluminescent compound has been dispersed. The device is further adapted to crush the frangible foam substrate upon the occurrence of a specific event.

These and other objects and advantages of the invention will become apparent and will be more fully set forth as the description thereof proceeds in the following specification and claims considered in connection with the attached drawings to which they relate.

BRIEF DESCRIPTION OF THE DRAWINGS

FIGS. 3–5 show the recorded output response of a photomultiplier tube set to record the light emission generated upon crushing one of the samples cored from the thickness of the molded sheet of porous foam of the present invention as well as the indicated stress in the sample recorded during the impact event.

In FIG. 3, no europate compound was incorporated into the foam sample. As can be seen, no light output is recorded as the sample is crushed.

FIG. 4 illustrates the recorded light emission behavior of porous samples incorporating 1% of the europate compound.

FIG. 5B thus shows a reduced but still very detectable light response, illustrating that the foam body is at least partially transparent/translucent to the light wavelength

FIG. 5C, therefore, demonstrates that the light response observed, as deployed in the foam body of the present invention, is not specific to the europate compound described herein but is observable in other materials.

DETAILED DESCRIPTION OF THE INVENTION

Figure 1:
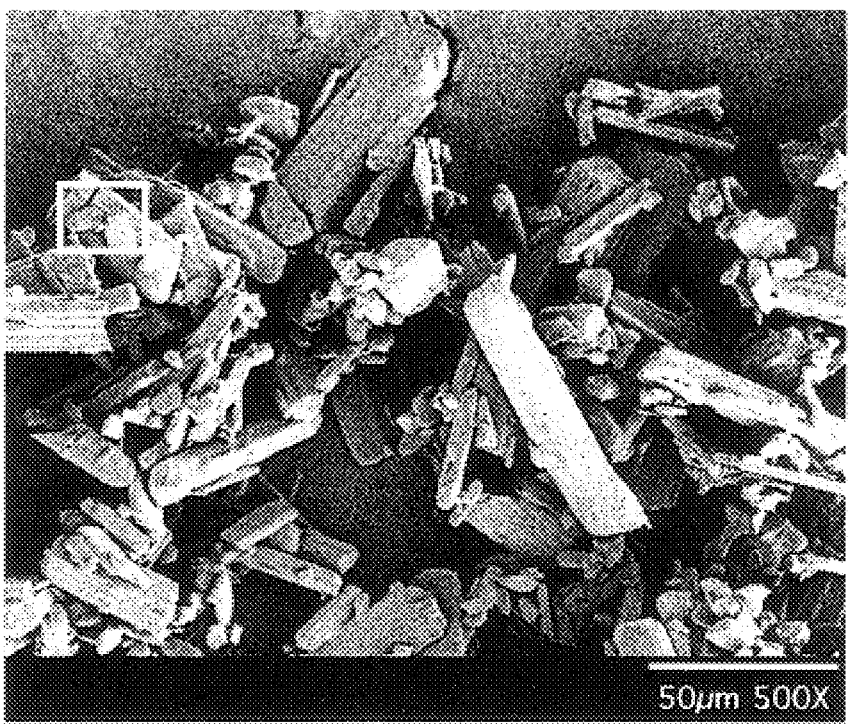
FIG. 1 shows a photomicrograph of crystals of the europate compound used in the present invention showing, in particular, the morphology of crystals recrystallized from a solution phase of the europate compound.
Figure 1:
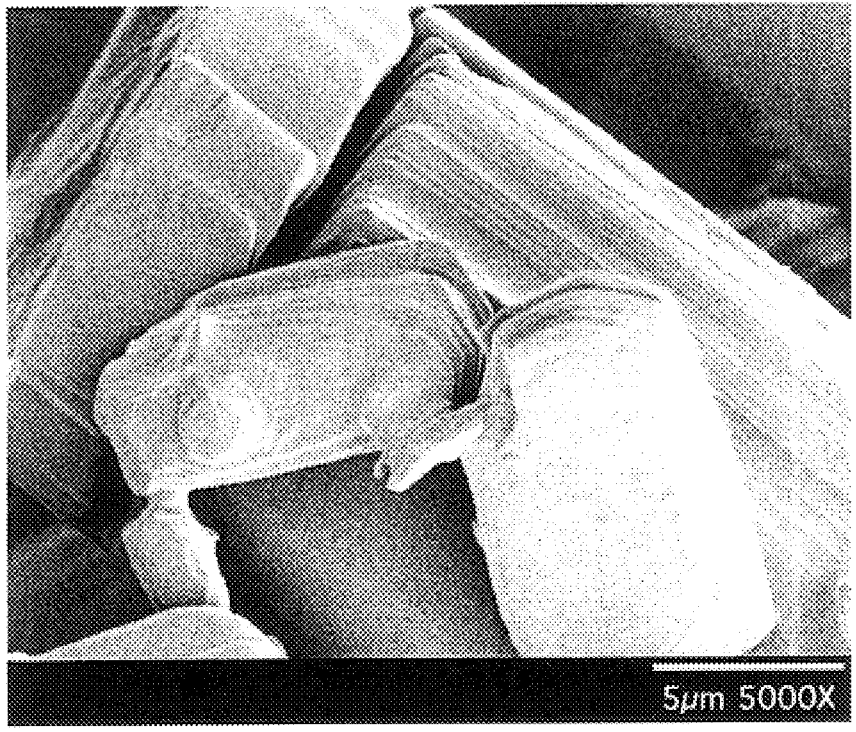

The following description of the invention is made with reference to the accompanying FIGURES. While various specific embodiments of the invention have been disclosed, it will be apparent that the invention is not limited to these embodiments, but may include other variations of an indicator device.

In particular, the present invention relies upon a brittle, porous body to be used as a carrier media for containing a triboluminescent material. Several classes of these materials are specifically comprehended herein, including polyurethane foams, syntactic foams comprised of glass micro-balloon filled epoxies, emulsion derived foams, such as the polymethacrylonitrile (PMAN), polyacrylonitrile (PAN), polystyrene homopolymers, or poly 4-methyl-1-pentene (TPX), and any other similar materials known to produce low density frangible bodies.

Also included and anticipated to provide similar benefits and utility are systems comprising a collection of glass micro-balloons bound together by a surface layer of adhesive which when molded or cast to shape provides a generally porous structure into which a triboluminescent material is incorporated. This may be accomplished by introducing a solution containing the triboluminescent material and subsequently precipitating that material into the interstitial spaces within the porous structure.

Formulation, Processing and Fabrication of a Brittle Polyurethane Foam

The foam chosen for the present invention was a rigid, closed-cell, water-blown polyurethane foam modified for the intended use, i.e., the foam was specifically formulated to be brittle. To prepare the foam, equal parts (5.2 grams each) of glycerol and a polyether polyol, 0.32 grams of a silicone surfactant, and 0.1 grams of an amine catalyst (such as trimethyl N',2-hydroxyethyl-propylenediamine), are mixed together with 0.36 grams of deionized (DI) water. The ingredients are combined in a small beaker and stirred with a metal spatula for approximately 2–4 minutes and the polyurethane foam reaction initiated as 39 grams of a polyisocyanate is added and thoroughly mixed for approximately 90 seconds. Once the isocyanate is added, the working time for the modified urethane foam is approximately 5 minutes, but can be adjusted for by varying the amount of catalyst. The mixture was then poured into an open metal mold and allowed to rise, polymerize and cross-link at room temperature. The material was then cured at 66° C. for 4 hours.

It should be noted that while the formulation described above is indicative of the porous material used to test for efficacy of the present invention, it should not be considered to in any way restrict the present invention nor should this formulation alone or for that matter to any other particular porous system. Furthermore, the above formulation can and does have a fair degree of tolerance associated with the percentage ranges for each of the constituents comprising the foam. The Table below lists the ranges over which the present invention is functional.

TABLE 1

WORKING RANGES FOR POLYURETHANE FOAM CONSTITUENTS

| COMPONENT | RANGE (%) |
| --- | --- |
| Voranol ® 490 | 10–15 |
| Voranol 490 is a trademark of The Dow Chemical Co. | |
| Glycerol | 10–15 |
| DC 193 ® Surfactant | 0.5–5 |
| DC 193 is a trademark of The Dow Chemical Co. | |
| Polycat 17 ® Catalyst | 0.1–3 |
| Polycat 17 is a trademark of The Air Products and Chemicals Corporation | |
| Deionized Water | 0.05–1 |
| Rubinate ® 1680 or Isonate ® 143-L | 60–90 |
| Rubinate 1680 is a trademark of The ICI Polyurethanes Group. Isonate 143 is a trademark of The Dow Chemical Co. | |
| Triboluminescent Particulates | 0.05–50 |

Selection and Charaterization of the Triboluminescent Powder

Various prior art references are made to a number of materials exhibiting triboluminescence. In particular, U.S. Pat. No. 4,020,765, herein incorporated by reference, recites various activated zinc compounds ($ZnF_2$:Mn, ZnS:Ag, ZnS:Mn), ZnCdS, zirconium-tin-alloys, and $CaP_2O_7$:Dy. More recently U.S. Pat. No. 6,071,632, herein incorporated by reference, refers to triboluminescence in a group of cyclic organic lanthanide compounds, particularly compounds of europium, terbium, dysprosium, and samarium. Finally, U.S. Pat. No. 5,905,260, also incorporated herein by reference, recites a list of organic compounds known to exhibit triboluminescence, noting particularly a citation in *Nature*, vol. 212, Oct. 8, 1966, pp.179–180 by C. R. Hurt, et al., that found that certain europium dibenzoylmethide chelates exhibited particularly intense triboluminescent emission.

Small amounts of the europium tetrakis (dibenzoylmethane) triethyl ammonium salt, therefore, were prepared as described by Hurt, et al., by combining triethylamine and dibenzoylmethane in hot ethanol. Europium trichloride, pre-dissolved in ethanol, was added and the resultant solution continuously stirred while cooling. The resultant precipitate was filtered, rinsed, and dried to provide a generally uneven distribution of slab-like particles ranging in size from about 10 to about 75 microns in length and about 3 to about 15 microns in width. As seen in FIG. 1 this material crystallizes into flat, terraced slabs having a generally rhombic morphology. The size distribution of the particles appears to be grouped into what constitute a single, broad distribution of particles ranging from about 5 to about 75 microns in length, and from about 2 to about 20 microns in width.

Formulation and Processing of the Eu—Filled Urethane Foam

The europium tetrakis(dibenzoylmethane) triethyl ammonium salt (hereinafter referred to as Eu(III)) was added to the polyol mixture, formulated in the manner described above, and stirred. The Eu(III) powder was added to the formulation after the glycerol, the polyol, the silicone surfactant, and the catalyst are mixed together with the deionized (DI) water had been combined and stirred together. The formulation was stirred until the powder was wetted and completely incorporated.

The polyurethane foam reaction was then initiated, as above, with the addition of the isocyanate after having combined and mixed the precursor constituents. The resultant liquid mixture was then poured into an open mold similar to the unfilled foam.

Figure 2:
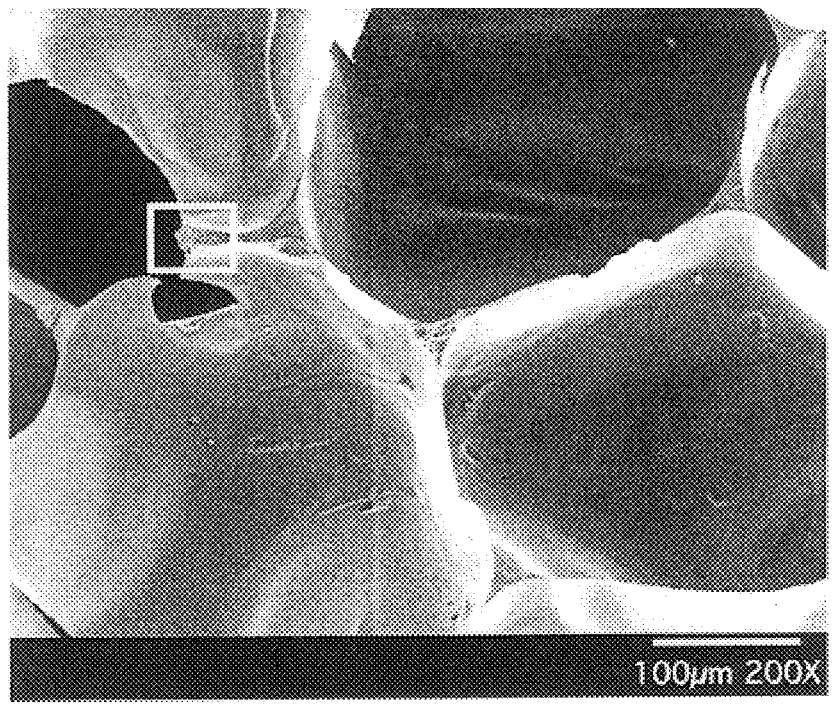
FIG. 2 shows a photomicrograph of a portion of the expanded foam which has been broken in two in order to expose an interior fracture surface and show at least one of the europate compound particles is embedded in one of the corner "struts" of the foam matrix.
Figure 2:
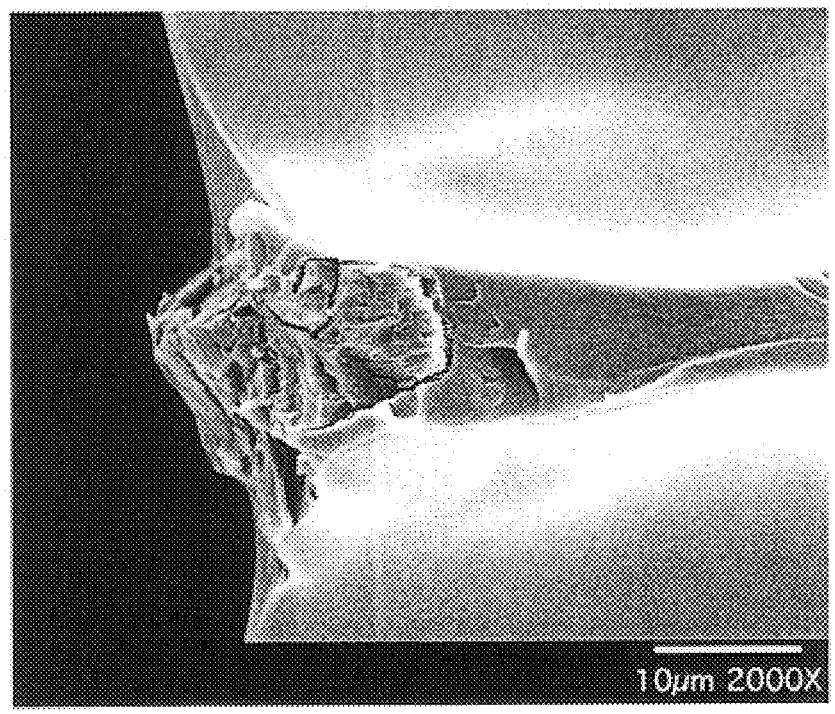

The weight percentage of Eu(III) powder added to the formulation was based on the total added weights of the four liquid constituents comprising the polyurethane mixture according to the following simple equation and irrespective of losses due to gas formation during the reaction:

$$100\left(\frac{x}{x+tot.}\right) = \text{wt. \%} \quad (1)$$

where:
  x=weight of filler to be added
  tot.=total weight of all liquid constituents
  wt. %=desired weight percent of filler present in the composite 1w/o, 2w/o, and 4w/o Eu(III) salt mixtures of the liquid polyurethane foam were prepared, cast in the same open mold, and cured at about 66° C. for approximately 4 hours. FIG. 2 shows a photomicrograph of a portion of the expanded foam which has been broken in two in order to expose an interior fracture surface. As can be seen, at least one, or a small number, of the Eu(III) particles is embedded in one of the corner "struts" of the foam matrix between three or more of the individual cells formed during the foam expansion phase. It is postulated that the particle fractured as the expanded portion of foam was broken and will therefore, presumably, behave in a similar manner whenever the foam matrix is fractured; whether crushed or simply flexed to failure.

Functional Characteristics of the Device

In order to test this hypothesis, right circular cylindrical samples 0.5" in diameter by 0.8" in height (12.7 mm ⌀×20.3 mm) were cut ("cored") from the molded foam sheet. For sample uniformity, care is taken to ensure that the samples do not contain any skin material from the surfaces of the sheet, cutting them to yield surfaces that were flat and parallel. The density of the resulting samples were determined to be about 0.07 g/cc.

Figure 3:
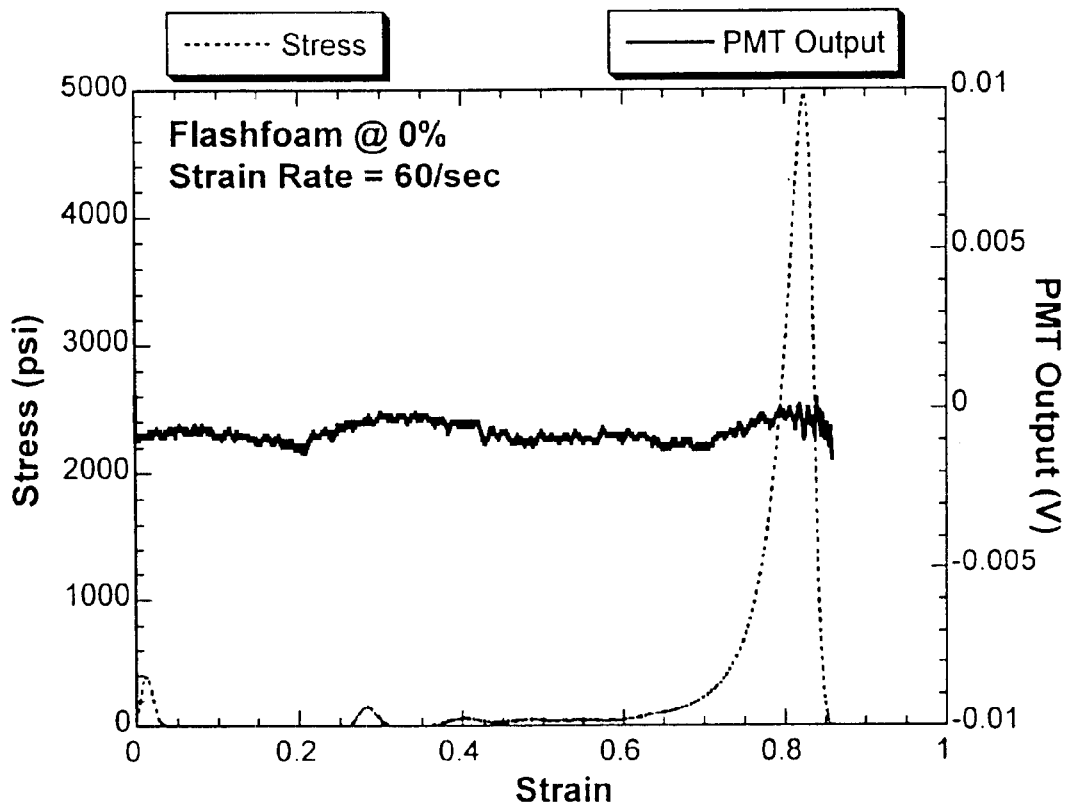
Figure 4:
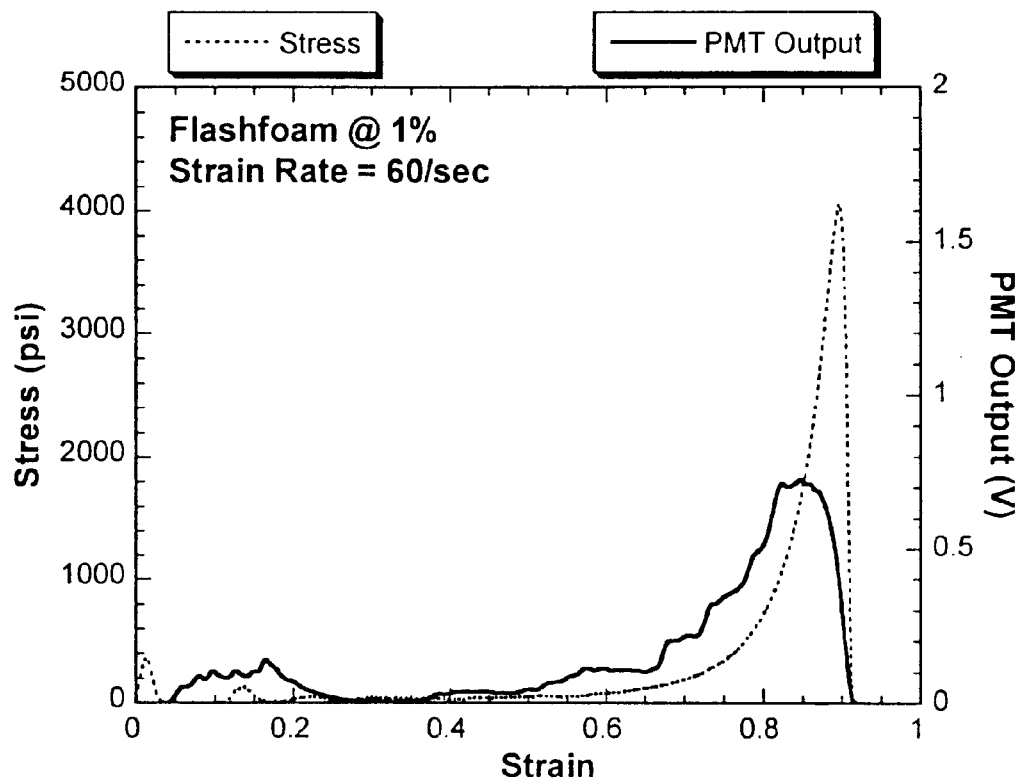
Figure 5A:
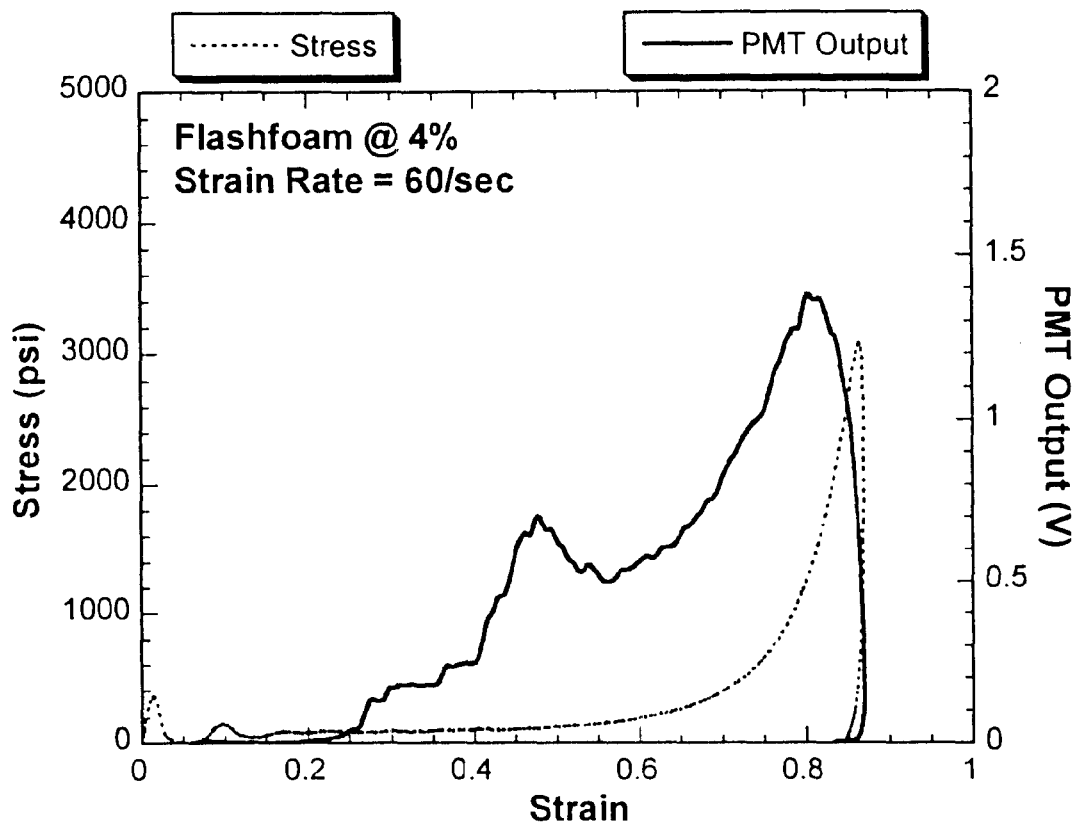
FIG. 5A illustrates the recorded light emission behavior of porous samples incorporating 4% of the europate compound. In addition, FIG. 5A also demonstrates that light emission increases with increasing europate content.
Figure 5B:
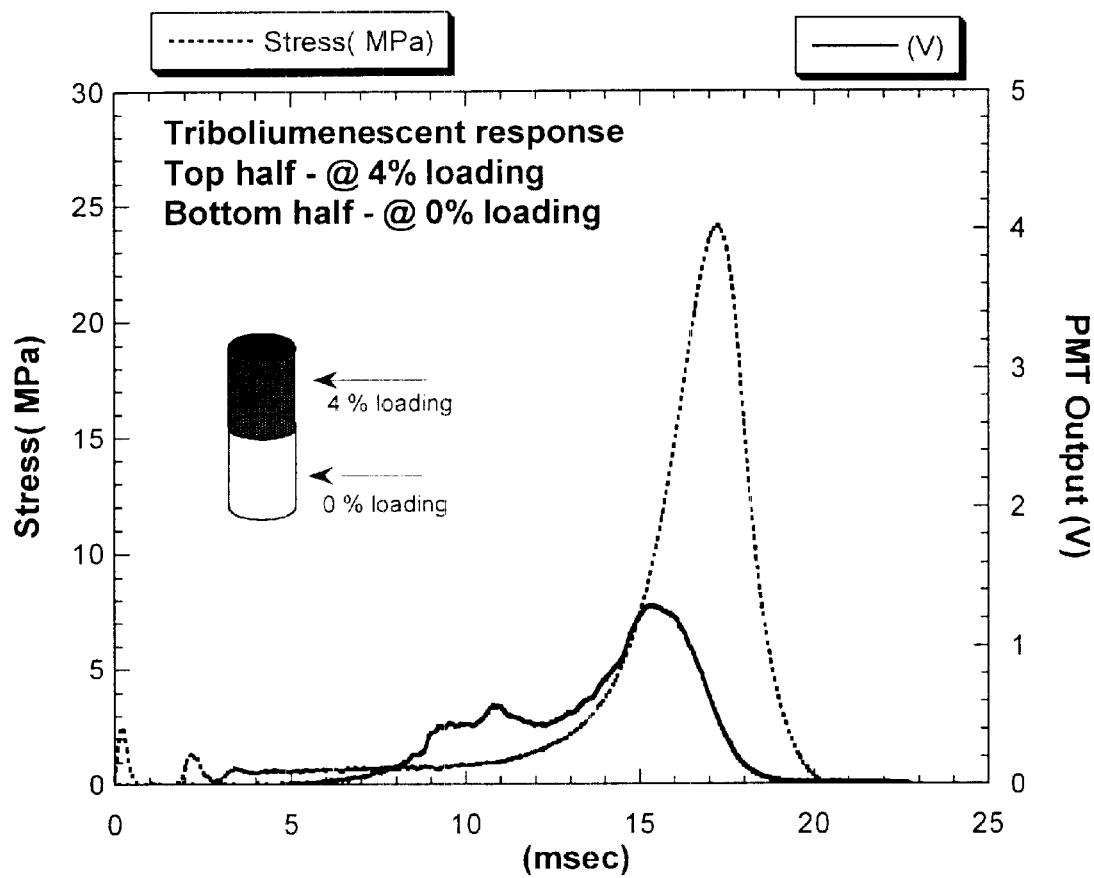
FIG. 5B illustrates the light response of a pair of stacked porous samples: the first sample placed directly adjacent to a light detection means contained no triboluminescent compound, while a second sample placed on top of the first and therefore displaced from the light detection means by the length of the first sample contained 4% of the europate compound.
Figure 5C:
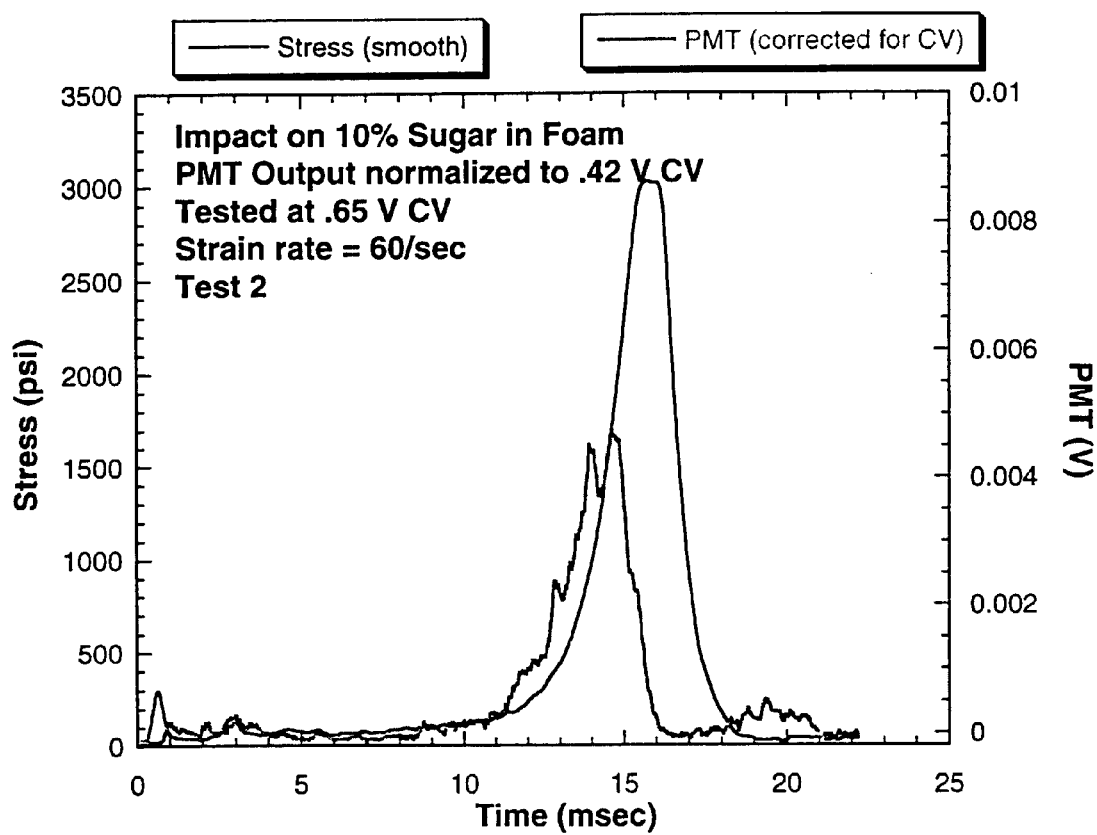
FIG. 5C illustrates the recorded light emission behavior of porous samples incorporating a quantity of sucrose, a known triboluminescent compound.

FIGS. 3, 4, and 5 show a series of exemplary output traces of a photomultiplier tube set up to capture and record the light emission generated upon crushing a sample of the porous foam. In the case of FIG. 3, none of the Eu(III) powder was incorporated into the foam and as can be seen from the Figure no light output is recorded as the sample is crushed. By way of contrast, FIGS. 4 and 5A and 5C however, illustrate the recorded light emission response of samples incorporating 1% and 4% of the Eu(III) powder. Very strong output signals are clearly indicated, and suggest that the speculated mechanical disruption of particles embedded with the foam is probably correct. It is noted also, that peak emission intensity as well as the cumulative emission output increase with increasing concentration of the Eu(III) additive.

FIG. 5B illustrates the light response of a pair of stacked samples of porous foam. A first sample, comprising a polyurethane foam body containing a 4% quantity of the europate triboluminescent powder, was placed on top of a second porous foam sample containing no triboluminescent powder. The two samples are then crushed together in order to illustrate that the foam body is at least partially transparent/translucent to the light emitted by the excited particles. FIG. 5B shows a reduced, but still very detectable, light response, illustrating that the foam body is indeed at least partially transparent/translucent to the emitted light wavelength and demonstrating that light produced within the bulk of the foam sample is being detected, and that the signal response that is measured is not restricted only to that portion of the foam directly adjacent to the detection device.

Finally, FIG. 5C shows the recorded light response of a polyurethane sample prepared with a sucrose powder showing that the sucrose emits light with the same temporal characteristics as the lanthanide material. This in turn illustrates that the configuration of the present invention is not restricted to the europate chelate in question but will generate light similarly as the chelate, albeit with different efficiency, so long as a triboluminescent compound is added.

First Embodiment

The present invention uses the triboluminescent effect to provide a passive, light emitting, signaling device. In designing such a device, however, it was desired to provide as small a system as possible while providing for as large, and reliable an output as was achievable. It was postulated that by dispersing a quantity of very small crystals of a triboluminescent material into a solid, suspension media and by providing a method for fracturing some substantial portion of those crystals, over some short time interval, there would be provided a device for generating a detectable quantity of light. It was therefore, determined to attempt to disperse a finely divided powder, of the chosen triboluminescent material, throughout a porous, expanded body—a foam suspension media.

The designed system comprised an opaque, hollow cylinder, closed at one end with a means for directing light into a communications conduit such as an optical fiber. Into this cylinder is placed a short cylindrical plug of the brittle foam, described above, containing the chosen triboluminescent powder dispersed throughout the foam matrix. The plug is fabricated to occupy between about ½–⅓ of the cylinder volume and is disposed against the closed end of the cylinder. The device is completed by inserting a plate, or piston means, on the end of the plug opposite the cylinder's closed end. The light emission is activated when the plate, or piston means, impacts the surface of the sample such that the body is rapidly crushed, thereby fracturing at least some portion of the particles of the triboluminescent material, such that those particles emit a detectable light emission pulse.

Figure 6A:
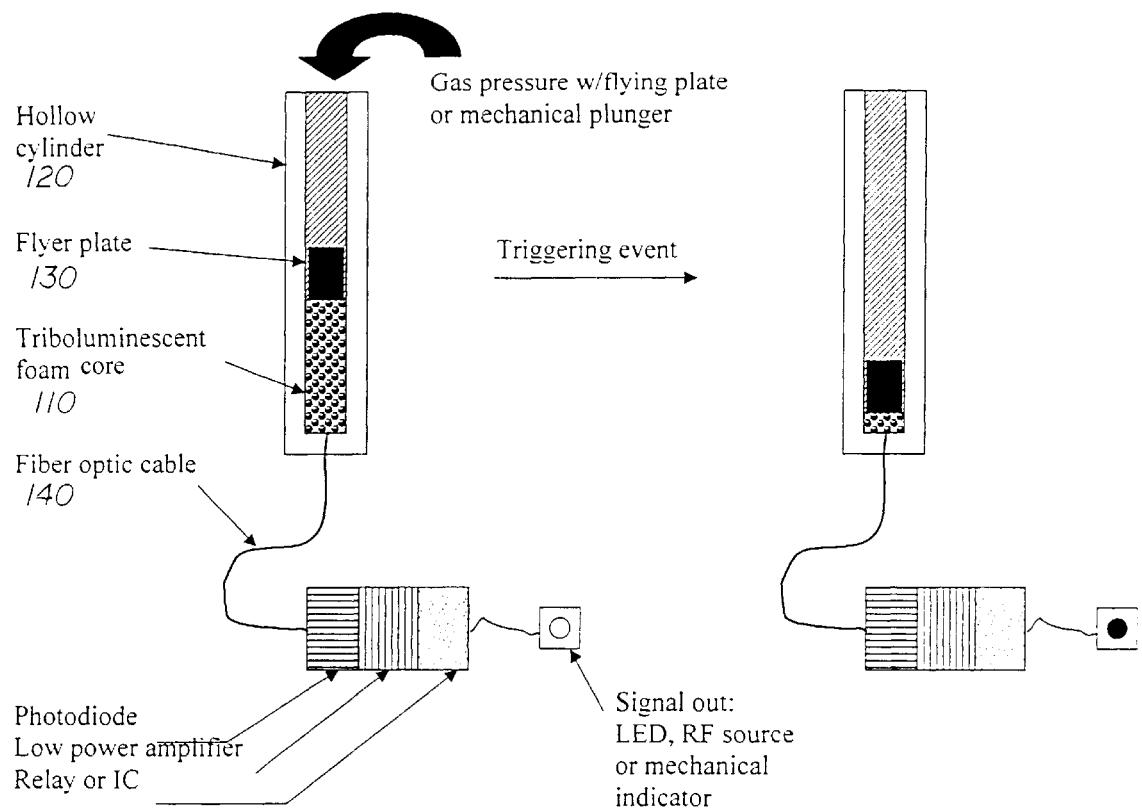
FIGS. 6A, 6B and 6C show various views of the indicator device of the present invention.

The present invention disclosed above is shown in FIG. 6A. A sample 110 of the triboluminescent foam body, prepared as described above, is placed into cylinder 120.

Plate, or piston means, 130 is placed in cylinder 120 and a linkage means (not shown) fixed to the piston or flyer-plate means 130 as a way so as to drive said means 130 onto sample 110 and thereby crushing it. This linkage means could be a free falling weight, or a compressible gas acting against piston means 130, a mechanical push rod linking the plate/piston means to a hydraulically actuated ram, or a releasably, triggered spring attached to, and released by, a second linkage mechanism responding to gradual systematic changes, finally accumulating to exceed a preset threshold value. Alternatively, a bistable spring which would eventually break away after exceeding a maximum stress could provide the motive power for driving the piston means onto the sample plug. Example of such systemic changes might be temperature, pressure, or multiple discrete events such as interval cycles of a clock mechanism.

Figure 6B:
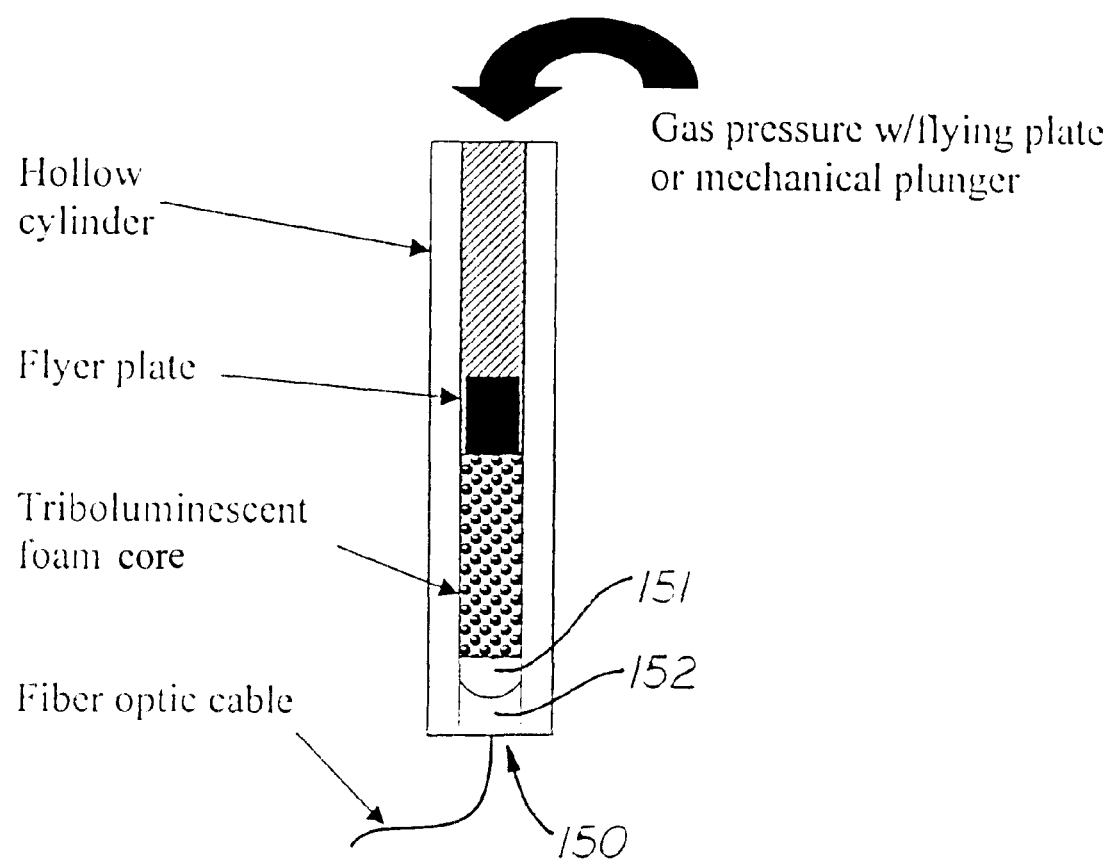

At the opposite end of cylinder 120, sample 110 is restrained by a closed end, which includes only a small hole to allow access for an optical fiber 140. Alternatively, as shown in FIG. 6B this end may include a lens 150, comprising for instance a condenser lens or a doublet lens, where the doublet lens would further comprise matched pair of lens consisting of a plano-convex lens 151 cemented to a plano-concave lens 152 wherein the convex portion of lens 151 faces toward an adjacent end 141 of fiber 140 which is itself glued to the flat, or "plano," end of concave lens 152. Lens 150 is then glued to the open end of cylinder 120 and used to focus more of the emitted light into optical fiber 140 which then would be coupled to photodiode or photomultiplier tube 160 in order to convert the detected light signal into an electrical pulse.

Figure 6C:
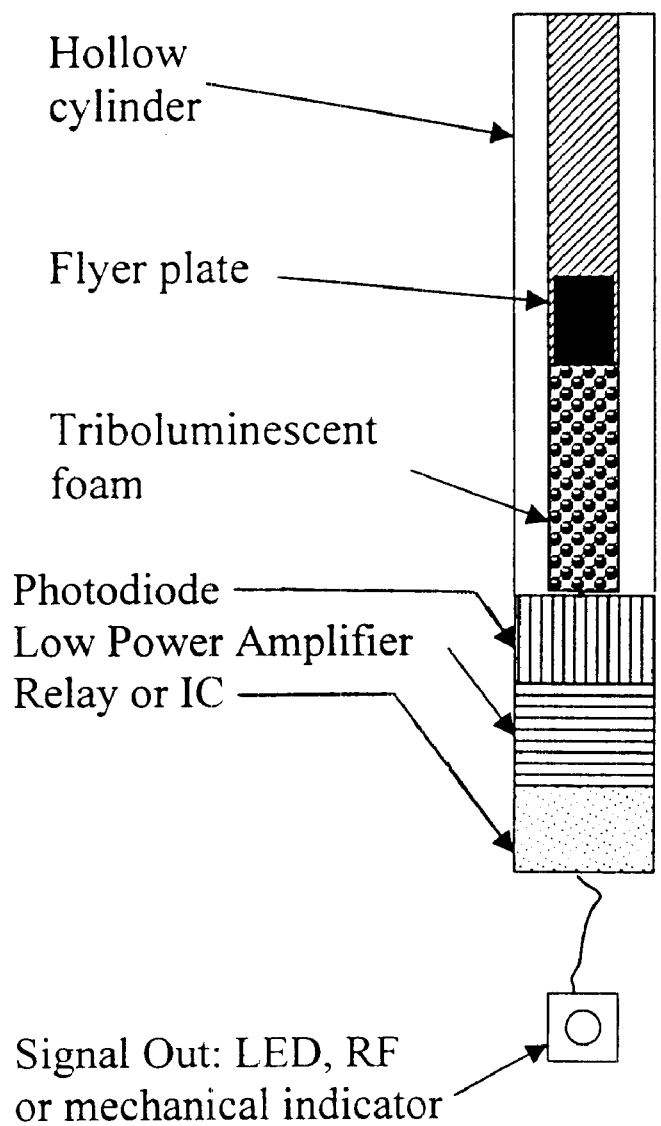

Also, alternatively, as shown in FIG. 6C this end may include a photodiode attached directly to cylinder 120. The effect of this arrangement is to couple the light energy of the triboluminescent effect directly into a electric pulse which may be communicated directly to a remote sensor or through an RF transmission.

Second Embodiment

The present invention is also deployed as a volume of foam of undefined size and shape into which a small amount of the triboluminescent material has been dispersed. Also dispersed and embedded throughout the foam body, and/or attached to its exterior surface are a plurality of small photodiodes, or some other sensible means for light detection. These devices are arranged and distributed such that each would encompass a detection volume sufficient in size to cover substantially all of the volume of foam into which the diodes/light detection devices are embedded. The diodes/light detection devices further comprise a means for responding to the transmitted light pulse signal, such as an electrical wire for conducting a resultant electrical pulse from the diode to an exterior indicator, or an RF transmitter for directly transmitting a signal pulse to a point outside the body. Furthermore, this means would optionally include a means for changing, or setting, a digital logic state for later analysis.

The foam body may therefore take the shape of any desired volume either inside or outside of a structure intending to be surveyed. Such uses as damage indicators for packing crates, pallets, vault structures, automotive/aircraft components, building structures, and the like.

The foregoing is but a brief description of a preferred embodiment. Those skilled in the art will appreciate that there exist many possible variations of this rudimentary design. Furthermore, it is appreciated that any triboluminescent material which is compatible with any frangible substrate comprehended by the foregoing description would be an effective substitute for the chelated europate recited herein and that any light detecting means would be effective at sensing the emitted light.

What is claimed is:

1. A light indicating assembly comprising:

a body comprising a brittle porous polymer foam;

a plurality of triboluminescent particles dispersed throughout said body;

a source of mechanical energy;

means for directing said mechanical energy onto at least a portion of said body, said means for directing disrupting and crushing said portion of said body and fracturing at least some portion of said triboluminescent particles; and a light sensing means.

2. The light indicating assembly of claim 1, further comprising a means for communicating said light pulse from a point adjacent to said body to said light sensing means.

3. The light indicating assembly of claim 2, wherein said light transmission means comprises an optical fiber.

4. The light indicating assembly of claim 1, wherein said light transmission means comprises an open aperture.

5. The light indicating assembly of claim 1, wherein said light sensing means comprises a transducer means for transforming electromagnetic radiation into an electrical current.

6. The light indicating assembly of claim 1, wherein said light sensing means is selected from the list consisting of photographic film, a photodiode, a photometer, a photomultiplier tube, a charge coupled device, an avalanche photodiode, and any other light sensing device or combination thereof.

7. The light indicating assembly of claim 1, wherein said light sensing means further comprises a means for collecting said light pulse.

8. The light indicating assembly of claim 7, wherein said means for collecting further comprises one or more lenses.

9. The light indicating assembly of claim 1, wherein said triboluminescent particles emit a detectable pulse of light as said particles are fractured.

10. The light indicating assembly of claim 9, wherein said triboluminescent particles are crystals selected from the group of materials consisting of lanthanide chelates.

11. The light indicating assembly of claim 10, wherein said crystals consist essentially of a europium tetrakis (dibenzoylmethane)triethyl ammonium salt.

12. The light indicating assembly of claim 1, wherein said polymer foam comprises a network of open or closed cells.

13. The light indicating assembly of claim 12, wherein said polymer foam is a low density foam.

14. The light indicating assembly of claim 1, wherein said polymer foam is a water—blown polyurethane foam.

15. The light indicating assembly of claim 1, wherein said means for directing said source of mechanical energy comprises:

a piston means contained within a cylinder, said cylinder comprising a smooth interior wall and one substantially closed end, said body contained within said cylinder between said piston means and said substantially closed end, said body extending substantially across a diameter of said cylinder; and drive means for driving said piston means onto said body such that said body is crushed at a strain rate in excess of 1 meters/meter/second.

16. The light indicating assembly of claim 15, wherein said piston means is a cylindrical disc, or plate, wherein said disc, or plate is arranged and disposed within said cylinder in order to move freely along an entire length of said cylinder.

17. The light indicating assembly of claim 16, wherein said piston means engages said interior wall so as to form a short term, near hermetic seal with said interior wall.

18. The light indicating assembly of claim 15, wherein said drive means comprises releasing stored chemical, mechanical, or hydraulic energy.

19. The light indicating assembly of claim 18, wherein said releasing said chemical energy comprises igniting a pyrotechnic match or ignitor.

20. The light indicating assembly of claim 18, wherein releasing said mechanical energy comprises releasing a compressed spring.

21. The light indicating assembly of claim 20, wherein said compressed spring is engaged by a ratchet-paw mechanism.

22. The light indicating assembly of claim 18, wherein releasing said hydraulic energy comprises pressurizing a fluid, wherein said fluid is a incompressible liquid or a compressed gas.

* * * * *